US00PP35628P2

(12) United States Plant Patent
Korlipara

(10) Patent No.: US PP35,628 P2
(45) Date of Patent: Jan. 30, 2024

(54) ***RUDBECKIA* PLANT NAMED 'LION CUB'**

(50) Latin Name: *Rudbeckia hirta*
Varietal Denomination: Lion Cub

(71) Applicant: Terra Nova Nurseries, Inc., Canby, OR (US)

(72) Inventor: Harini Korlipara, Tualatin, OR (US)

(73) Assignee: Terra Nova Nurseries, Inc., Candy, OR (US)

( * ) Notice: Subject to any disclaimer, the term of this patent is extended or adjusted under 35 U.S.C. 154(b) by 0 days.

(21) Appl. No.: 18/215,262

(22) Filed: Jun. 28, 2023

(51) Int. Cl.
*A01H 5/02* (2018.01)
*A01H 6/14* (2018.01)

(52) U.S. Cl.
USPC ..... Plt./474

(58) Field of Classification Search
USPC ..... Plt./263.1, 474
See application file for complete search history.

*Primary Examiner* — Karen M Redden
(74) *Attorney, Agent, or Firm* — The Webb Law Firm

(57) ABSTRACT

A new and distinct *Rudbeckia* plant having cupped to quilled, golden-colored ray florets, a short, rounded habit, and excellent vigor.

2 Drawing Sheets

Botanical classification: *Rudbeckia hirta.*
Varietal denomination: 'Lion Cub'.

BACKGROUND OF THE NEW PLANT

The present invention is a new and distinct *Rudbeckia* plant having the varietal name 'Lion Cub'. *Rudbeckia* is in the family Asteraceae. 'Lion Cub' is a selection from a planned breeding program that originated from a controlled cross between unnamed, unpatented, and proprietary *Rudbeckia hirta* seedlings. The seed parent has a small habit with semi-double, yellow-orange flowers. The pollen parent has a medium habit with semi-double, gold flowers.

Compared to the annual *Rudbeckia* plant named 'Maya' (unpatented), the new cultivar is more gold colored than yellow and is more consistent in height and flower form. Compared to *Rudbeckia* plant named 'Henry Eilers' (unpatented), 'Lion Cub' is an annual, not a perennial, has fully double flowers and is much shorter than 'Henry Eilers'.

The new variety has only been reproduced by asexual propagation (cuttings and tissue culture). Each of the progeny exhibits identical characteristics to the original plant. Asexual propagation by cuttings and tissue culture using standard micropropagation techniques with terminal and lateral shoots performed in Canby, Oregon shows that the characteristics and distinctions described herein come true to form and are established and transmitted through succeeding propagations. The present invention has not been evaluated under all possible environmental conditions. The phenotype may vary with variations in environment without a change in the genotype of the plant.

When compared to other *Rudbeckia* plants known to the breeder, the new variety is characterized by the following:

1. Inflorescences with cupped to quilled, golden-colored ray florets;
2. A short, rounded habit; and
3. Excellent vigor.

DESCRIPTION OF THE DRAWINGS

The accompanying photographic drawings illustrate the new variety at approximately 6 months of age, with the colors being as nearly true as possible with color illustrations of this type.

DETAILED BOTANICAL DESCRIPTION

Figure 1:
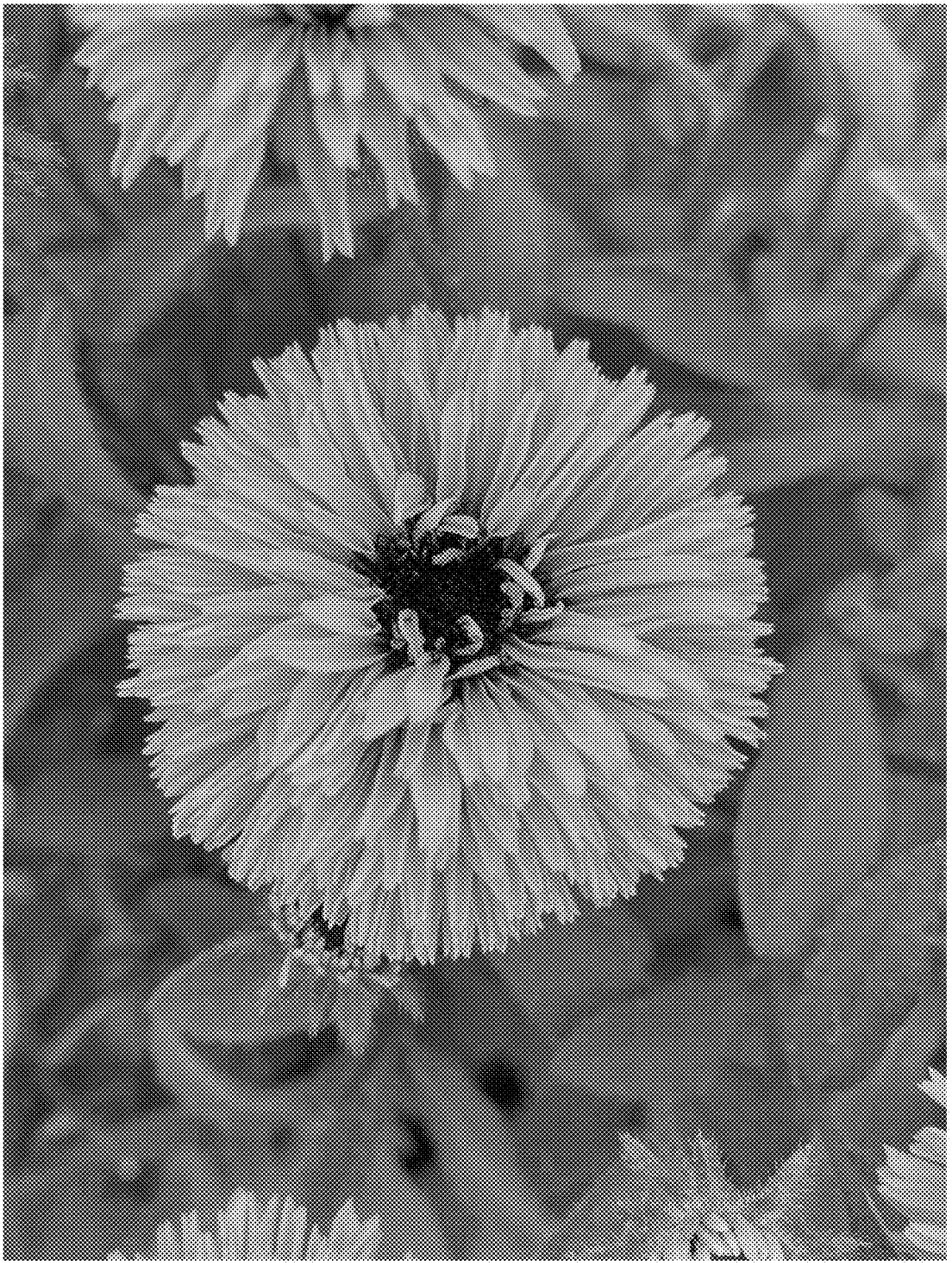
FIG. 1 illustrates a close-up view of the new variety in Canby, Oregon.
Figure 2:
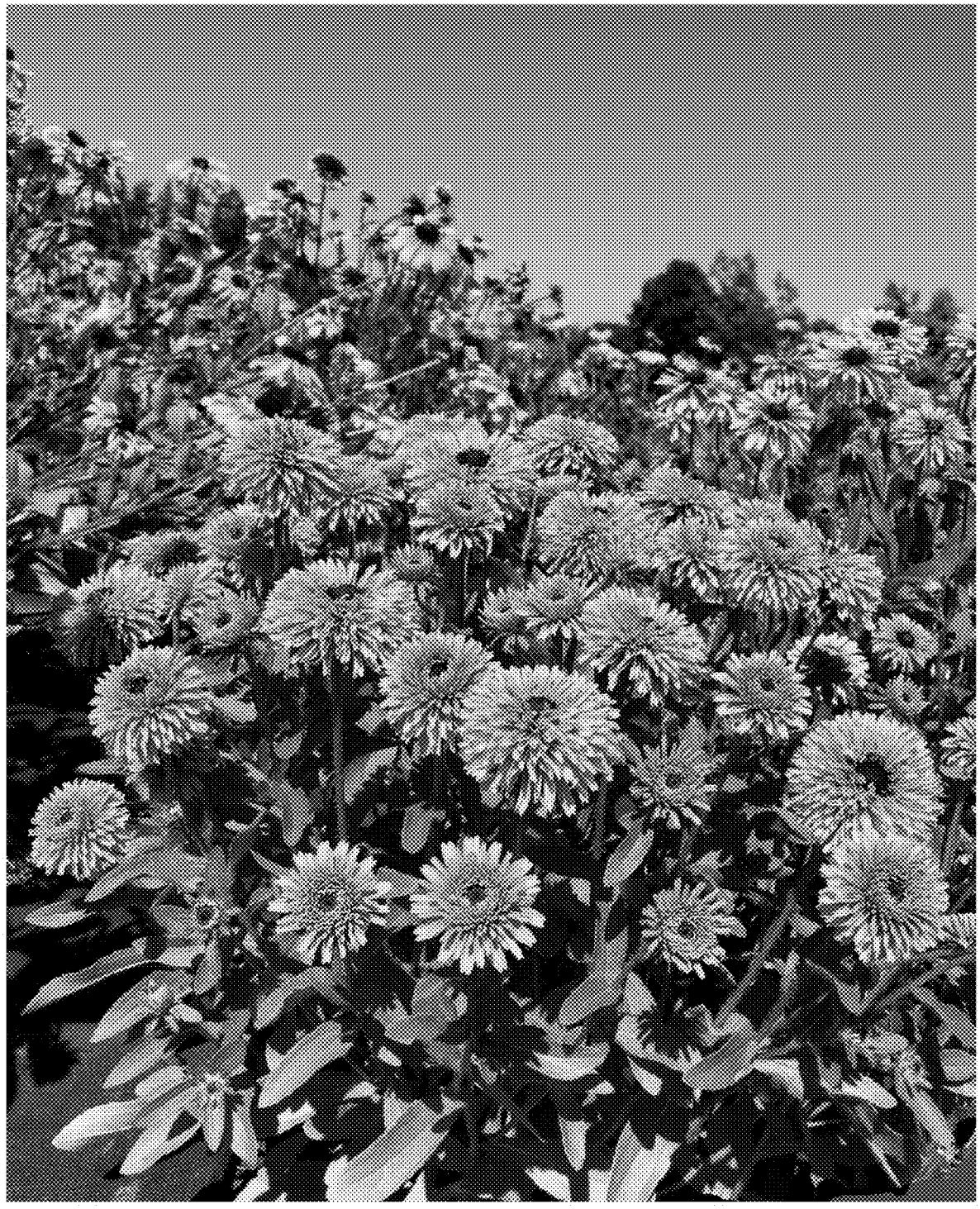
FIG. 2 illustrates plants of the new variety in the field in full sun in Canby, Oregon in early October.

The following is a detailed description of the new variety based on observations of 6-month-old plants that were grown outside under full sun in Canby, Oregon (USDA Zone 8). Temperatures range from a high of 35° C. in August to a low of 0° C. in January. Normal rainfall in Canby, Oregon is around 1 m per year. Color references are based on The 2007 R.H.S. Colour Chart of The Royal Horticultural Society of London, 5$^{th}$ Edition.

Plant:
- *Type.*—Herbaceous annual.
- *Hardiness.*—USDA Zones annual.
- *Size.*—40.0 cm wide and 40.0 cm tall from the top of the soil to the top of the inflorescences.
- *Form.*—Basal clump, with about 20 stems from the base.
- *Vigor.*—High.

Flowering stems:
- *Type.*—Ascending, branching where flowering only.
- *Inflorescences per stem.*—From 3 to 15.
- *Size.*—About 6.0 cm tall to the start of a flowering branch and 3.0 to 3.5 cm wide at the base.
- *Internode length.*—From 3.0 cm to 5.0 cm.
- *Texture.*—Strigose.
- *Color.*—RHS 145A, with thin, vertical bands of RHS 146C present.

Leaf:
- *Type.*—Simple.
- *Arrangement.*—Alternate.
- *Shape.*—Cuneate to lanceolate.
- *Size.*—Overall to 6.5 cm long and 2.3 cm wide, terminal leaflets grow to 7.5 cm long and 5.0 mm wide, and lateral leaflets grow to 4.0 cm long and 2.0 cm wide.

*Margin*.—Serrate.
*Apex*.—Acute.
*Base*.—Attenuate.
*Texture*.—Strigose on both sides.
*Venation*.—Pinnate, with 3 main veins extending from the base on each leaflet.
*Upper surface color*.—RHS 137B, with venation color of RHS N137B.
*Lower surface color*.—RHS 137D, with venation color of RHS N137B.
*Petiole*.—Length: To 2.5 mm. Width: 1.5 mm, measured above the clasp. Texture: Strigose. Color: RHS 145C.

Inflorescence:
*Type*.—Composite.
*Number of flowering branches from stem*.—3 to 15.
*Flowering stem*.—Grows to 35.0 cm tall from the start of the flowering branches to the base of the terminal inflorescence and 5 to 10 side branches grow to 4.0 cm taller than the terminal inflorescence. The cluster of inflorescences grows to 12.0 cm long and 10.0 cm wide. The leaves on the flowering branches are simple, ovate in shape, and grow to 7.5 cm long and 2.5 cm wide. Their margins are serrate, base attenuate, tip acute, and have an upper surface color of RHS 137B, lower surface color of 137D, and venation color of RHS N137B.
*Width*.—To 6.5 cm.
*Depth*.—1.5 cm.
*Form*.—Ray florets are held mostly horizontally and a mature disc is rounded.
*Bloom period*.—May through October in Canby, Oregon.
*Lastingness on the plant*.—About 2-3 weeks in Canby, Oregon.
*Fragrance*.—None.
*Fertility*.—Moderate.

Flower bud (immature inflorescence):
*Form*.—Ray florets held upright and tubular.
*Width*.—2.5 cm.
*Depth*.—2.0 cm.
*Color*.—Ray florets: RHS 151B and tinted RHS N144C. Disc: RHS 203B.

Ray florets:
*Number*.—From 24 to 30.
*Shape*.—Linear and cupped, with the apex being 5-lobed — each lobe is ovate in shape, with entire margins and acute tips.
*Length*.—2.3 cm.
*Width*.—4.5 to 5.0 mm.
*Margin*.—Entire.
*Texture*.—Upper surface: Pubescent. Inner surface: Glabrous.
*Color* (*both surfaces*).—RHS N167D at the base, with the apex being RHS 163B. The bottom surface has a tint of RHS 163B present at the base.
*Pistil*.—None.
*Stamen*.—None.

Disc/disc florets:
*Disc*.—Shape: Rounded. Depth: To 12.0 mm. Width: To 12.0 mm. Color: RHS 203B.
*Disc florets*.—Number: About 450 and bisexual. Shape: 5-lobed (triangular lobes) with a tubular, glandular corolla. Overall length: 6.0 mm. Overall width: 1.5 mm. Corolla length: 3.0 mm. Corolla width: 1.5 mm. Color: RHS N186B. Pistil: 1; 7.0 mm long; RHS N186D. Ovary: 3.0 mm long; RHS NN155B. Style: 4.0 mm long; RHS N186B. Stigma: 2-branched; RHS 187A. Stamen: 5; 7.0 mm long; RHS 187A. Pollen: RHS 17A.

Phyllaries:
*Description*.—3 leafy series that grow in area to 2.6 cm wide and 5.0 mm deep.
*Lobes*.—Shape: Lanceloate and slightly reflexed. Length: 9.0 mm. Width: 3.0 mm. Color (both sides): RHS 139A. Margin: Entire. Apex: Acuminate. Texture (both sides): Strigose.

Receptacle:
*Width*.—10.0 mm.
*Depth*.—8.0 mm.
*Color*.—RHS 146B.

Seeds:
*Length*.—2.0 mm.
*Width*.—0.75 mm.
*Color*.—RHS 203B.

Pests/diseases: No unusual resistance or susceptibility noted to date.

I claim:

1. A new and distinct variety of *Rudbeckia* plant named 'Lion Cub', substantially as illustrated and described herein.

* * * * *